US010679742B2

(12) United States Patent
Gotman et al.

(10) Patent No.: US 10,679,742 B2
(45) Date of Patent: Jun. 9, 2020

(54) VECTOR-VALUED DIAGNOSTIC IMAGE ENCODING

(71) Applicant: KONINKLIJKE PHILIPS N.V., Eindhoven (NL)

(72) Inventors: Shlomo Gotman, Haifa (IL); Nadav Hanan Shapira, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/307,652

(22) PCT Filed: May 17, 2018

(86) PCT No.: PCT/EP2018/062977
§ 371 (c)(1),
(2) Date: Dec. 6, 2018

(87) PCT Pub. No.: WO2018/211027
PCT Pub. Date: Nov. 22, 2018

(65) Prior Publication Data
US 2020/0098468 A1 Mar. 26, 2020

(30) Foreign Application Priority Data
May 17, 2017 (EP) ..................................... 17171578

(51) Int. Cl.
*G16H 30/40* (2018.01)
*G06T 9/00* (2006.01)
(Continued)

(52) U.S. Cl.
CPC ........... *G16H 30/40* (2018.01); *G06K 9/6255* (2013.01); *G06K 9/6267* (2013.01);
(Continued)

(58) Field of Classification Search
USPC ...................... 382/128, 131, 253; 375/240.22
See application file for complete search history.

(56) References Cited

U.S. PATENT DOCUMENTS 6,404,923 B1 * 6/2002 Chaddha ................. G06T 9/008
382/224
7,283,857 B1 10/2007 Fallor
(Continued)

OTHER PUBLICATIONS

Siddiqui, et al., "Multi Stage Vector Quantization for the Compression of Surface and Volumetric Point Cloud Data", Signal Processing and Information Technology, 2007 IEEE.
(Continued)

*Primary Examiner* — Ishrat I Sherali
(74) *Attorney, Agent, or Firm* — Larry Liberchuk

(57) ABSTRACT

The invention relates to an image processing device (10) for processing diagnostic image data, comprising: a data input (11) for receiving vector-valued diagnostic image data and a quantification unit (12) for, for each pixel, determining a subset of identifiers, selected from a predetermined set of template identifiers, and determining for each identifier of the subset a quantification value indicative of a presence, proportion or significance in the pixel of a material or condition corresponding to the identifier. The device comprises a dictionary definition unit (14) for providing a dictionary that assigns an index to each unique identifier subset, and an image data encoder (16) for encoding the image data. The encoder is adapted for, for each pixel, calculating a bit sequence comprising a first set of bits encoding the index and further sets of bits encoding quantification values. The device also comprises a data packager (18) for packing the encoded image in a diagnostic image format and for inserting the dictionary into metadata of that format. Further aspects relate to a decoding device, a system,
(Continued)

corresponding methods for encoding and decoding and derived computer related products.

13 Claims, 3 Drawing Sheets

(51) Int. Cl.
G06T 7/00 (2017.01)
G06T 7/62 (2017.01)
G06K 9/62 (2006.01)
G16H 30/20 (2018.01)

(52) U.S. Cl.
CPC .............. *G06T 7/0012* (2013.01); *G06T 7/62* (2017.01); *G16H 30/20* (2018.01); *G06K 2209/05* (2013.01); *G06T 2200/24* (2013.01); *G06T 2207/10081* (2013.01); *G06T 2207/10088* (2013.01); *G06T 2207/20101* (2013.01); *G06T 2207/20104* (2013.01)

(56) References Cited

U.S. PATENT DOCUMENTS

| | | | | |
|---|---|---|---|---|
| 8,442,289 B2 * | 5/2013 | Kadomura | ............ | A61B 6/032 382/128 |
| 9,639,933 B2 * | 5/2017 | Liang | ................... | G06T 7/0012 |
| 2005/0031181 A1 | 2/2005 | Bi | | |
| 2006/0280348 A1 * | 12/2006 | Smith | ................... | G06T 7/0012 382/128 |
| 2010/0014627 A1 * | 1/2010 | Wang | ..................... | H03M 7/30 378/4 |
| 2010/0014729 A1 | 1/2010 | Choi | | |
| 2010/0166273 A1 * | 7/2010 | Wismuller | ............ | G06T 7/0012 382/131 |
| 2010/0205142 A1 | 8/2010 | Feulner | | |
| 2015/0301141 A1 * | 10/2015 | Griswold | ........... | G01R 33/5608 382/131 |
| 2016/0123904 A1 | 5/2016 | Masood | | |
| 2017/0324983 A1 * | 11/2017 | Fenney | ................ | H04N 19/426 |
| 2018/0165809 A1 * | 6/2018 | Stanitsas | ............... | G06F 3/0484 |
| 2019/0122073 A1 * | 4/2019 | Ozdemir | ................ | G06N 20/00 |

OTHER PUBLICATIONS

Gaudeau, et al., "Lossy Compression of Volumetric Medical Images with 3D Dead Zone Lattice Vector Quantization", Picture Coding Symposium, 2007.

Chen, et al., "Automatic Quality Control for Wavelet-Based Compression of Volumetric Medical Images Using Distortion-Constrained Adaptive Vector Quantization", IEEE Transaction on Medical Imaging, 2004.

Mendonga et al, "A Flexible Method for Multi-Material Decomposition of Dual-Energy CT Images", IEEE Transactions on Medical Imaging 33(1), pp. 99-116.

ISO standard 12052:2006 "Health informatics—Digital imaging and communication in medicine (DICOM) including workflow and data management."

* cited by examiner

VECTOR-VALUED DIAGNOSTIC IMAGE ENCODING

CROSS REFERENCE TO RELATED APPLICATIONS

This application is the U.S. National Phase application under 35 U.S.C. § 371 of International Application No. PCT/EP2018/062977, filed May 17, 2018 published as WO 2018/211027 on Nov. 22, 2018, which claims the benefit of European Patent Application Number 17171578.2 filed May 17, 2017. These applications are hereby incorporated by reference herein.

FIELD OF THE INVENTION

The invention relates to the field of digital image processing, e.g. diagnostic image processing. More specifically it relates to an image processing device for processing diagnostic image data, an image decoding device and related methods.

BACKGROUND OF THE INVENTION

Medical image data, such as computed tomography (CT) image data, nuclear medicine image data and magnetic resonance (MR) image data, are commonly stored, e.g. encoded, in a standard image format for medical images, for example in accordance with a DICOM image format standard, e.g. in accordance with the NEMA DICOM PS3 standard, for example as specified in the NEMA DICOM PS3 2017a specification, and/or in accordance with the ISO standard 12052:2006 "Health informatics—Digital imaging and communication in medicine (DICOM) including workflow and data management."

It is also known in the art that specific medical imaging technologies generate non-scalar image data, thus comprising a plurality of separate values, e.g. forming a vector value, for each image voxel (or pixel) location. These separate values may be indicative of different material properties of the imaged subject, or, at least, convey different or complementary information about the same imaged pixel or voxel location.

For example, in multi-energy CT imaging, e.g. spectral CT imaging or dual-energy CT imaging, different materials can be identified by analyzing multi-energy data acquired during the CT scanning. Thus, each pixel in the generated CT image may have pixel values associated therewith that correspond to one or more materials or chemical elements that can be identified, by applying, for example, material decomposition and related techniques known in the art. Furthermore, various properties of the materials, such as a mass fraction or a number of material units in each pixel (or voxel) can be calculated.

It is known in the art to handle material-specific data by generating and viewing DICOM-compatible images for each scalar component of such non-scalar, i.e. vector-valued, image data, e.g. each material, separately.

For example, the United States patent application no. US 2010/0014729 discloses a method for separating diagnostic content of x-ray images from non-diagnostic content to achieve an image reproduction and windowing. A plurality of radiological density images may be displayed, in accordance with a disclosed method, in a single viewing window by overlaying greyscale images of each radiological density image in a single display window.

SUMMARY OF THE INVENTION

It is an object of embodiments of the present invention to provide efficient methods and means for storing, transmitting and/or visualizing diagnostic image data.

The above objective is accomplished by a method and device according to the present invention.

It is an advantage of embodiments of the present invention that vector-valued diagnostic image information, e.g. material-specific properties relating to a plurality of different materials, can be efficiently stored, e.g. with a low storage overhead, in a standard image format, e.g. a DICOM format.

It is an advantage of embodiments of the present invention that vector-valued diagnostic image information, e.g. material-specific properties relating to a plurality of different materials, can be easily visualized, e.g. for individual pixels (or voxels) and/or a selected region of interest in the image.

It is an advantage of embodiments of the present invention that efficient data storage of diagnostic images can be achieved, e.g. of diagnostic images comprising vector-valued pixel or voxel information.

It is an advantage of embodiments of the present invention that efficient data transmission, e.g. network transfer, of diagnostic images can be achieved, e.g. of diagnostic images comprising vector-valued pixel or voxel information.

For example, storing vector-valued image data, e.g. data relating to different materials, in separate DICOM-compatible images for each scalar component of the vector-valued image data, as known in the art, may impose significant data storage and network transfer overheads, e.g. when the images are stored in archives and/or transferred over a data communication network, e.g. between medical institutions. For example, this may impose a significant burden on a Picture Archiving and Communication System (PACS) for storing and transferring medical image data. It is an advantage of embodiments of the present invention that such overheads may be reduced.

It is an advantage of embodiments of the present invention that a user may easily view and assess complementary information, e.g. relating to different materials, in diagnostic images comprising vector-valued pixel or voxel information. For example, in an image storage method as known in the art, different scalar components of such vector-valued image data may be stored and visualized substantially separately, e.g. independently. Thus, a user might be required to examine multiple sets of images to assess material content of various anatomical areas, in accordance with a method as known in the art. A typical diagnostic tomographic image, e.g. a CT scan, can consist of hundreds of images, such that the burden on the user could be significant, e.g. which may be, particularly, a substantial burden when evaluating vector-valued image data, e.g. spectral image data, in accordance with a method as known in the art. It is an advantage of embodiments of the present invention that such burden on the user may be reduced.

In a first aspect, the present invention relates to an image processing device for processing, e.g. encoding and packing, diagnostic image data. The image processing device comprises a data input for receiving vector-valued diagnostic image data, e.g. via a data communication network and/or via a physical data carrier.

The image processing device comprises a quantification unit for, for each image coordinate of a plurality of image coordinates in the diagnostic image data, e.g. for each for each pixel or voxel location, determining a subset of identifiers, selected from a predetermined set of template identifiers, based on the received vector-valued diagnostic image data and for determining, for each identifier of the subset of identifiers, a corresponding quantification value indicative of a presence, a proportion and/or a significance at the image coordinate of a material or condition corresponding to the identifier.

The image processing device comprises a dictionary definition unit for providing a dictionary, the dictionary definition unit being adapted for assigning a subset identification index to each unique subset of identifiers that is determined by the quantification unit for the vector-valued diagnostic image data and for including a definition of each of the assignations in the dictionary.

The image processing device comprises an image data encoder for encoding the diagnostic image data such as to provide an encoded image, the image data encoder being adapted for, for each image coordinate, calculating a bit sequence, such that a first set of bits of the bit sequence encodes the subset identification index assigned to the subset of identifiers determined for the image coordinate and such that further sets of bits of the bit sequence respectively encode quantification values determined for the image coordinate.

The image processing device comprises a data packager for packing the encoded image in a diagnostic image format comprising metadata, and for inserting the dictionary into the metadata.

In an image processing device in accordance with embodiments of the present invention, the data input may be adapted for receiving spectral computed tomography volumetric image data, magnetic resonance volumetric image data and/or nuclear medicine tomography volumetric image data.

In an image processing device in accordance with embodiments of the present invention, the plurality of template identifiers may comprise template identifiers representative of different materials and/or chemical elements.

In an image processing device in accordance with embodiments of the present invention, the quantification unit may comprise a material decomposition processor for determining properties of different materials based on the vector-valued diagnostic image data for each image coordinate such as to determine the quantification value as a value indicative of a volume fraction of a material identified by the identifier in a volume represented by the image coordinate.

In an image processing device in accordance with embodiments of the present invention, the plurality of template identifiers may comprise template identifiers indicative of air, adipose tissue, soft tissue, a radiocontrast agent, e.g. iodine, and bone.

In an image processing device in accordance with embodiments of the present invention, the quantification unit may be adapted for determining the subset of identifiers by selecting the subset from a plurality of template subsets of the plurality of template identifiers, e.g. a predetermined plurality of predetermined template subsets of predetermined template identifiers.

In an image processing device in accordance with embodiments of the present invention, each of the plurality of template subsets may comprise a same number of template identifiers.

In an image processing device in accordance with embodiments of the present invention, the image data encoder may be adapted for determining the first set of bits as a binary representation of the subset identification index in a number of bits equal to the least succeeding integer greater than or equal to the base-2 logarithm of the number of template subsets in the plurality of template subsets.

In an image processing device in accordance with embodiments of the present invention, the image data encoder may be adapted for determining the further sets of bits of the bit sequence by encoding the quantification values in an order defined by the dictionary, wherein each further set of bits consists of a number of bits equal to the least succeeding integer greater than or equal to the base-2 logarithm of the inverse of a precision value.

In an image processing device in accordance with embodiments of the present invention, the quantification unit may be adapted for determining the quantification values such that the sum of the quantification values determined for each subset of identifiers equals a predetermined value.

In an image processing device in accordance with embodiments of the present invention, the further sets of bits may encode the quantification values for all but one identifier in the determined subset of identifiers, e.g. all but the last identifier in the determined subset of identifiers.

In an image processing device in accordance with embodiments of the present invention, the data packager may be adapted for applying a compression algorithm to compress the encoded image and for including the compressed encoded image in the diagnostic image format.

In an image processing device in accordance with embodiments of the present invention, the data packager may be adapted for generating an output diagnostic image in the diagnostic image format, wherein the diagnostic image format may be compliant with a DICOM standard.

Embodiments of the present invention may also relate to a Picture Archiving and Communication System or diagnostic image portal system comprising an image processing device in accordance with embodiments of the present invention.

In a second aspect, the present invention also relates to an image decoding device for decoding diagnostic image data packed in a diagnostic image format comprising metadata, e.g. in a DICOM format. The image decoding device may be adapted for decoding an image generated by a device in accordance with embodiments of the first aspect of the present invention. For example, a device in accordance with embodiments of the first aspect of the present invention and a device in accordance with embodiments of the second aspect of the present invention may be considered as two interrelated products, e.g. that complement each other and/or work together.

The image decoding device comprises a data input for receiving the packed diagnostic image data, e.g. via a data communication network and/or via a physical data carrier, e.g. from a device in accordance with embodiments of the first aspect of the present invention.

The image decoding device comprises a data unpackager for unpacking an encoded image from the packed diagnostic image data and for unpacking a dictionary from metadata in the packed diagnostic image data.

The image decoding device comprises an image data decoder for decoding the encoded image such as to provide diagnostic image data, the image data decoder being adapted for, for each image coordinate, retrieving a bit sequence from the encoded image, identifying a subset of identifiers by looking up, in the dictionary, a subset identification index, encoded in a first set of bits of the bit sequence and for determining quantification values, assigned to the identifiers of the subset, from further sets of bits of the bit sequence.

The image decoding device comprises a mapping unit for generating a map for each identifier referenced in the dictionary, each map comprising the quantification values assigned to the corresponding identifier by the image data decoder to represent a presence, a proportion and/or a significance at each image coordinate of a material or condition corresponding to the identifier.

In an image decoding device in accordance with embodiments of the present invention, the image data decoder may be adapted for determining the quantification values by decoding further sets of bits of the bit sequence that encode quantification values in an order defined by the subset of identifiers in the dictionary, and for computing a further quantification value for a last identifier in the subset of identifiers by subtracting the sum of the quantification values encoded in the further sets of bits from a predetermined value.

An image decoding device in accordance with embodiments of the present invention may comprise a processing unit for attributing further physical properties to each image coordinate based on the maps generated by the mapping unit.

An image decoding device in accordance with embodiments of the present invention may comprise a visualization unit for showing a visual representation of at least one of the maps to a user, in which the visualization unit is adapted for providing a graphical user interface to the user for viewing the visual representation.

In an image decoding device in accordance with embodiments of the present invention, the visualization unit may be adapted to enable the user to select a specific point and/or a region of interest on the visual representation, for selecting a homogeneous region in the selected region of interest and/or around the selected point, for extracting data from the maps and/or from the further physical properties, corresponding to the selected homogeneous region, and for presenting a material classification and/or quantification statistical information relating to the selected homogeneous region to the user.

Embodiments of the present invention may also relate to a workstation comprising an image decoding device in accordance with embodiments of the present invention.

In a third aspect, embodiments of the present invention also relate to a spectral computed tomography system comprising an image processing device in accordance with embodiments of the first aspect of the present invention and/or an image decoding device in accordance with embodiments of the second aspect of the present invention.

In a fourth aspect, the present invention relates to a method for processing diagnostic image data. The method comprises obtaining vector-valued diagnostic image data, e.g. CT image data, such as spectral CT image data, MR image data and/or nuclear medicine image data. The method comprises, for each image coordinate of a plurality of image coordinates in the diagnostic image data, determining a subset of identifiers, selected from a predetermined set of template identifiers, based on the received vector-valued diagnostic image data. The method comprises determining for each identifier of the subset of identifiers a corresponding quantification value indicative of a presence, a proportion and/or a significance at the corresponding image coordinate of a material or condition corresponding to the identifier.

The method also comprises providing a dictionary by assigning a subset identification index to each unique subset of identifiers that is determined by the quantification unit for the vector-valued diagnostic image data.

The method furthermore comprises encoding the diagnostic image data such as to provide an encoded image, in which, for each image coordinate, a bit sequence is calculated, such that a first set of bits of the bit sequence encodes the subset identification index assigned to the subset of identifiers determined for the image coordinate and further sets of bits of the bit sequence respectively encode quantification values determined for the image coordinate.

The method comprises packing the encoded image in a diagnostic image format comprising metadata and including the dictionary in the metadata.

In a fifth aspect, the present invention also relates to a method for decoding diagnostic image data packed in a diagnostic image format comprising metadata. The method comprises obtaining packed diagnostic image data and unpacking respectively an encoded image from the packed diagnostic image data and a dictionary from the metadata. The method furthermore comprises decoding the encoded image such as to provide diagnostic image data, in which, for each image coordinate, a bit sequence is retrieved from the encoded image, a subset of identifiers is identified by looking up a subset identification index, encoded in a first set of bits of the bit sequence, in the dictionary, and quantification values assigned to the identifiers are determined from further sets of bits of the bit sequence.

The method also comprises generating a map for each identifier referenced in the dictionary, each map comprising the quantification values assigned to the corresponding identifier by the image data decoder to represent a presence, a proportion and/or a significance at each image coordinate of a material or condition corresponding to the identifier. Such method in accordance with embodiments of the present invention may also comprise visualizing at least one of the generated maps.

In a sixth aspect, embodiments of the present invention also relate to a computer program product for, if implemented on a processing unit, performing a method in accordance with embodiments of the present invention, e.g. a method in accordance with embodiments of the fourth and/or fifth aspect of the present invention.

In a seventh aspect, embodiments of the present invention also relate to a data carrier storing a computer program product in accordance with embodiments of the sixth aspect of the present invention.

In an eighth aspect, embodiments of the present invention also relate to a transmission of a computer program product in accordance with embodiments of the sixth aspect of the present invention over a digital communication network.

In a ninth aspect, embodiments of the present invention also relate to an encoded image in a diagnostic image format comprising metadata, wherein the metadata comprises a dictionary for assigning subset identification indices to a plurality of unique subsets of identifiers, and wherein the encoded image further comprises, e.g. in a compressed or uncompressed form, a bit sequence for each of a plurality of image coordinates, e.g. for each pixel or voxel in the image. The bit sequence comprises a first set of bits encoding a subset identification index for assigning one of the subsets of identifiers to that image coordinate, and further sets of bits that respectively encode quantification values determined for that image coordinate. Each quantification value is indicative of a presence, a proportion and/or a significance at the corresponding image coordinate of a material or condition corresponding to the identifier it is associated with, e.g. indicative of a volume fraction in a voxel corresponding to the image coordinate of a material corresponding to the identifier.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
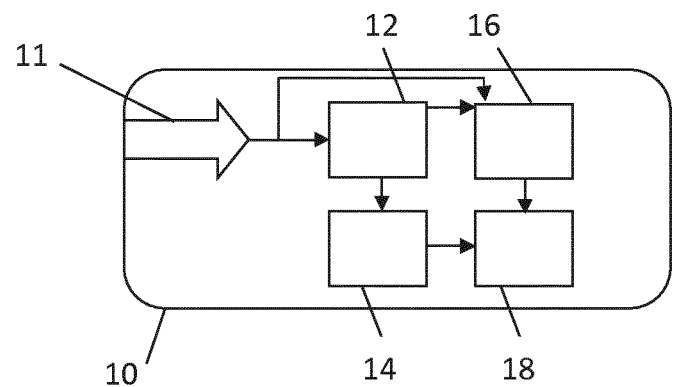
FIG. 1 schematically illustrates an image processing device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to a "pixel", reference is made to a value attributed to a specific location in a two-dimensional, three-dimensional, four-dimensional image or generally multi-dimensional image, e.g. to a specific location as defined by at least two, e.g. three spatial coordinate components, e.g. different coordinate components of a coordinate system. The location may be defined by optionally including a further non-spatial coordinate component (or plurality thereof) in addition to the spatial coordinate components, e.g. a time coordinate. Specifically, a "pixel" may also refer to a "voxel," but is not necessarily limited to three-dimensional voxels. A pixel location, e.g. a voxel location, in the image may be generally referred to as an "image coordinate".

Where in embodiments of the present invention, reference is made to "vector-valued," reference is made to data in which, to each coordinate in a domain, e.g. in a range in a spatial or temporal-spatial space over which the data is defined, a vector value is assigned, e.g. consisting of an ordered set of scalar component values, e.g. particularly more than one such scalar value. The different scalar component values of such vector value, e.g. of each vector value in such data, may represent different physical, chemical and/or material properties, e.g. may be representative of different materials or different combinations of materials, at a same location in the input coordinates domain.

In a first aspect, embodiments of the present invention relate to an image processing device for processing diagnostic image data, e.g. a medical image. The image processing device comprises a data input for receiving vector-valued diagnostic image data. For example, in the diagnostic image data, a plurality of scalar component values may be attributed to each of a plurality of image coordinates, e.g. to each pixel or voxel location, in which these scalar components are representative of different physical, chemical and/or material properties of an imaged object at a location corresponding to the image coordinate, e.g. a pixel coordinate, e.g. a voxel coordinate.

The image processing devices comprises a quantification unit for, for each image coordinate of a plurality of image coordinates in the diagnostic image data, e.g. over which image coordinates the diagnostic image data is defined, determining a subset of identifiers, selected from a predetermined larger set of template identifiers, i.e. the larger set consisting of a larger number of template identifiers than the number of identifiers of the subset. This subset of identifiers is determined based on the vector-valued diagnostic image data. The quantification unit is furthermore adapted for determining, for each identifier of the subset of identifiers, a corresponding quantification value indicative of a presence, a proportion and/or a significance at that image coordinate of a material or condition corresponding to that identifier, e.g. based on the vector-valued diagnostic image data.

The image processing device furthermore comprises a dictionary definition unit for providing a dictionary. The dictionary definition unit is adapted for assigning a subset identification index to each unique subset of identifiers that is determined by the quantification unit for the vector-valued diagnostic image data and for including a definition of each of these assignations in the dictionary.

The image processing device also comprises an image data encoder for encoding the diagnostic image data such as to provide an encoded image. The image data encoder is adapted for, for each of said plurality of image coordinates, calculating a bit sequence such that a first set of bits of the bit sequence encodes the subset identification index assigned to the subset of identifiers determined for that image coordinate and further sets of bits of the bit sequence respectively encode quantification values determined for that image coordinate.

The image processing device comprises a data packager for packing the encoded image in a diagnostic image format comprising metadata, and for inserting the dictionary into the metadata.

Referring to FIG. 1, an image processing device 10 for processing diagnostic image data, e.g. a medical image, is shown.

The image processing device 10 comprises a data input 11 for receiving vector-valued diagnostic image data. For example, in the diagnostic image data, a plurality of scalar component values may be attributed to each of a plurality of image coordinates, in which these scalar components are representative of different physical, chemical and/or material properties of an imaged object at a location corresponding to the image coordinate, e.g. a pixel coordinate, e.g. a voxel coordinate.

The diagnostic image data may convey anatomical information regarding anatomy of a subject. The different scalar components of the vector-valued diagnostic image data may convey different anatomical information, e.g. complementary anatomical, physiological and/or functional information, e.g. each component conveying at least some information that is not conveyed by any other scalar component.

The data input 11 may be adapted for receiving radiology image data. For example, the data input 11 may be adapted for receiving computed tomography volumetric image data, e.g. spectral computed tomography image data, such as dual-energy computed tomography image data, and/or magnetic resonance volumetric image data, e.g. magnetic resonance spectroscopy image data. The data input may be adapted for receiving nuclear medicine tomography volumetric image data, e.g. the vector-valued data relating to emissions of different radio-isotopes at a same pixel or voxel location.

The image processing devices comprises a quantification unit 12 for, for each image coordinate of a plurality of image coordinates in the diagnostic image data, e.g. over which image coordinates the diagnostic image data is defined, determining a subset of identifiers, selected from a predetermined larger set of template identifiers, i.e. consisting of a larger number of template identifiers than the number of identifiers in the subset.

The plurality of template identifiers may comprise template identifiers representative of different materials and/or chemical elements and/or conditions, such as conditions relating to physiology, metabolism and/or disease at the location in the body of an imaged subject corresponding to the image coordinate.

The subset of identifiers is determined based on the vector-valued diagnostic image data. The quantification unit 12 may determine the subset of identifiers, e.g. a sequence of m identifiers, e.g. material identifiers, for each pixel.

For example, for each image coordinate, e.g. for each pixel location, e.g. for each voxel in a volumetric diagnostic image, such as a CT image, the quantification unit may be adapted to identify subset of identifiers indicative of materials contained in the imaged object at a location represented by that image coordinate, e.g. a subset selected from a list of $N_m$ known materials, e.g. where $N_m > m$.

For example, the plurality of template identifiers may comprise, for example, template identifiers indicative of air (e.g. identified as "Air"), adipose tissue (e.g. identified as "Fat"), soft tissue (e.g. identified as "Tissue"), a radiocontrast agent (e.g. iodine, e.g. identified as "Iodine") and bone (e.g. identified as "Bone"), e.g. thus defining $N_m = 5$ template materials, embodiments of the present invention not necessarily being limited to such specific exemplary identifiers.

The quantification unit 12 may be adapted for selecting one such subset of identifiers for each pixel from a set of S template identifier sets, e.g. from a list of S template subsets of template identifiers, e.g. a list of material sequences. The quantification unit 12 may be adapted for, for each image coordinate of a plurality of image coordinates in the diagnostic image data, determining the subset of identifiers selected from the predetermined larger set of template identifiers, in which the subset may be selected from a plurality of template subsets of the template identifiers. For example, each pixel, or voxel, may be identified with a specific sequence, e.g. a sequence deemed most appropriate, of m materials from a predetermined set of material sequences, e.g. a set of S material sequences.

Each of the plurality of template subsets may comprise a same number m of template identifiers, where $m < N_m$, however embodiments of the present invention are not necessarily limited to template subsets having the same number of elements.

In the exemplary set of template identifiers described hereinabove, the plurality of template subsets may, for example, embodiments of the present invention not being limited thereto, comprise the ordered sets {"Air","Tissue", "Iodine"}, {"Air","Tissue","Fat"}, {"Tissue","Fat","Bone"} and {"Tissue","Iodine","Bone"}, e.g. thus forming S=4 template combinations of the template identifiers, each template combination consisting of m=3 identifiers of the $N_m$=5 predetermined template identifiers. For example, the plurality of template subsets may comprise all combinations of m elements selected from the $N_m$ template identifiers, but embodiments of the present invention are not limited thereto, as per the example given hereinabove. For example, the number of template subsets may be less than the total number of possible combinations, e.g.

$$\binom{N_m}{m}$$

in accordance with the binomial formula.

The quantification unit 12 is furthermore adapted for determining, for each identifier of the subset of identifiers, a corresponding quantification value indicative of a presence, a proportion and/or a significance at that image coordinate of a material or condition corresponding to that identifier, e.g. based on the vector-valued diagnostic image data.

For example, the quantification value may be indicative of a volume fraction of a material, identified by the identifier, in a volume represented by the image location, e.g. in the pixel or voxel.

The quantification unit 12 may comprise a material decomposition processor for determining properties of different materials based on the vector-valued diagnostic image data, e.g. densities and/or relative volumes, e.g. volume fractions, for each image coordinate, e.g. for each image pixel. For example, the material decomposition processor may be adapted for performing a material decomposition technique for spectral CT imaging, e.g. multi-energy or dual-energy CT imaging, as known in the art.

For example, embodiments of the present invention may use methods known in the art to identify, for each voxel of a received CT image, a subset of materials, e.g. represented in the form of the subset of identifiers, from a list of known materials, e.g. represented in the form of the plurality of template identifiers, contained in that voxel.

The quantification unit may be adapted for determining the quantification values such that the sum of the quantification values determined for each subset of identifiers equals a predetermined value, e.g. a unit value, e.g. 1. For example, the quantification values may be representative of volume fractions that sum to 1, indicative of the volume unit of the pixel or voxel.

The quantification unit may be adapted for selecting the subset and determining the quantification values by applying a numeric optimization, e.g. selecting the subset as a best fit for the corresponding set of quantification values, e.g. taking an optimization cost function and/or potential function into account.

The quantification unit may be adapted for selecting the subset and determining the quantification values by inferring a likely composition at the image location, for example by applying an image segmentation. The quantification unit may be adapted for selecting the subset and determining the quantification values by taking non-local information into account, e.g. by taking neighboring image locations into account and/or by taking a global position of the image location into account, for example relative to detected image landmarks.

The quantification unit may be adapted for selecting the subset and determining the quantification values by applying a combination of a numeric optimization, e.g. selecting the subset as a best fit of the image information at the image location in the diagnostic image data for the corresponding set of quantification values and non-local image information, e.g. by applying a maximum-a-posteriori method, e.g. by applying a Markov Random Field method.

The quantification unit may be adapted for implementing a method as disclosed in "A Flexible Method for Multi-Material Decomposition of Dual-Energy CT Images", by Mendonça et al, in IEEE TRANSACTIONS ON MEDICAL IMAGING 33(1), pp. 99-116.

The image processing device furthermore comprises a dictionary definition unit 14 for providing a dictionary. The dictionary definition unit 14 is adapted for assigning a subset identification index to each unique subset of identifiers that is determined by the quantification unit for the vector-valued diagnostic image data and for including a definition of each of these assignments in the dictionary.

For example, the subset of identifiers, e.g. a material sequence, may be selected, for each pixel, from a number S of template subsets of the template identifiers, e.g. from S material sequences, e.g. each numbering a number m of material identifiers, and a unique identifying index (UII) may be assigned to each unique sequence. A sequence dictionary may thus be defined to be stored within the metadata as described hereinbelow.

For example, a unique identifying index (UII) may be assigned to each template subset, e.g. each template sequence, and a complete sequence dictionary may be defined. For example, in the example given hereinabove, a dictionary could be defined as presented in the table hereinbelow:

UII Material Sequence
0 {"Air","Tissue","Iodine"}
1 {"Air","Tissue","Fat"}
2 {"Tissue",Fat","Bone"}
3 {"Tissue","Iodine","Bone"}

While the order of template identifiers in each template subset may be relevant for the encoding and decoding processes, as described further hereinbelow, this does not necessarily have an impact on the information storing capability or accuracy of the method. The dictionary definition unit 14 may also be adapted for determining an encoding precision, e.g. a precision for each template identifier in each template subset. For example, the precision may preferably be determined by the dictionary definition unit 14, or predetermined, such as not to exceed a precision of a material classification and quantification algorithm implemented by the quantification unit. For example, the precision may have a direct impact on the size of the resulting stored data. For example, the precision, e.g. each precision, may be determined as $p=2^{-x}$ where x is an integer. For example, for x=8, the precision may be of $2^{-8}$=0.0039, e.g. representative of a quantum of volume fraction of 0.0039.

The dictionary definition unit 14 may be adapted for actively assigning a subset identification index to each unique subset of identifiers that is determined by the quantification unit for the vector-valued diagnostic image data, or may comprise a passive data structure, e.g. a static and/or predetermined data structure representative of the dictionary. Likewise, the precisions may be actively determined by the dictionary definition unit, or may be predetermined and/or passively implemented, e.g. by data stored in a static data structure or hard-coded in a code for implementing the image data encoder.

The image processing device also comprises an image data encoder 16 for encoding the diagnostic image data such as to provide an encoded image. The image data encoder 16 is adapted for, for each of said plurality of image coordinates, calculating a bit sequence such that a first set of bits of the bit sequence encodes the subset identification index assigned to the subset of identifiers determined for that image coordinate and further sets of bits of the bit sequence respectively encode quantification values determined for that image coordinate.

For example, while the first set of bits not necessarily refers to bits at a start of the bit sequence, in accordance with embodiments of the present invention, this may be the case in some embodiments. For example, the first ceiling($\log_2 S$) bits (or another predetermined subrange of the bit sequence consisting of ceiling($\log_2 S$) bits) may correspond to the unique identifying index (UII) of the selected subset of identifiers for the image coordinate. In the example provided hereinabove, the selected subset of the S=4 template subsets may be referenced by two bits in each bit sequence.

The further sets of bits of the bit sequence may encode the quantification values, e.g. in an order defined by the corresponding dictionary entry. For example, each further set of bits may consist of ceiling($\log_2 p^{-1}$) bits, where p refers to a precision assigned to the particular identifier in the template subset of template identifiers, a precision assigned to all identifiers in common in the template subset of template identifiers, or a precision assigned to all identifiers in all template subsets in common.

A further set of bits may be included in the bit sequence for each identifier in the template subset. For example, the total number of bits in the bit sequence may be ceiling($\log_2 S$)+m·ceiling($\log_2 p^{-1}$).

Preferably, where the quantification unit is adapted for determining the quantification values such that the sum of the quantification values determined for each subset of identifiers equals a predetermined value, e.g. 1, the further set of bits may include all but one, e.g. the last, identifier in the template subset. For example, since the quantification values may sum to a predetermined value, one quantification value may be excluded from the encoding, the corresponding quantification value being determinable when decoding by subtraction of the sum of the encoded quantification values from the predetermined value. For example, the total number of bits in the bit sequence may be ceiling($\log_2 S$)+(m−1)·ceiling($\log_2 p^{-1}$).

For the example provided hereinabove, with S=4 material sequences each consisting of m=3 materials and a selected precision of $2^{-8}$ volume fraction, the number of encoded bits for each voxel may be ceiling($\log_2 4$)+(3−1)·ceiling($\log_2 2^8$)=2+2×8=18 bits.

The image data encoder 16 may advantageously provide an optimized encoding of multiple materials present in the diagnostic image.

The image processing device comprises a data packager 18 for packing the encoded image in a diagnostic image format comprising metadata, and for inserting the dictionary, provided by the dictionary definition unit 14 into the metadata.

The data packager 18 may be adapted for applying a compression algorithm to compress the encoded image and including the compressed encoded image in the diagnostic image format.

The data packager 18 may be adapted for packing the encoded image in a standard diagnostic image format comprising metadata, e.g. compatible with a prior-art image format standard for diagnostic images.

The diagnostic image format may be a diagnostic image format compliant with a DICOM standard, e.g. a NEMA DICOM standard, e.g. in accordance with the NEMA DICOM PS3 standard, for example as specified in the NEMA DICOM PS3 2017a specification, and/or in accordance with the ISO standard 12052:2006 "Health informatics—Digital imaging and communication in medicine (DICOM) including workflow and data management."

The image processing device may be a Picture Archiving and Communication System (PACS) and/or diagnostic image portal system. For example, embodiments of the present invention may relate to a Picture Archiving and Communication System (PACS) and/or diagnostic image portal system comprising an image processing device in accordance with embodiments of the first aspect of the present invention. Such PACS or portal system may be adapted for storing diagnostic image data and/or for transferring diagnostic image data over a digital communication network.

In a second aspect, the present invention relates to an image decoding device for decoding diagnostic image data packed in a diagnostic image format comprising metadata, e.g. as provided by embodiments of the first aspect of the present invention. The image decoding device comprises a data input for receiving the packed diagnostic image data and a data unpackager for unpacking an encoded image from the packed diagnostic image data and a dictionary from metadata in the packed diagnostic image data. The image decoding device comprises an image data decoder for decoding the encoded image such as to provide diagnostic image data. The image data decoder is adapted for, for each image coordinate, retrieving a bit sequence from the encoded image, identifying a subset of identifiers by looking up a subset identification index, encoded in a first set of bits of the bit sequence, in the dictionary, and for determining quantification values assigned to the identifiers of that subset of identifiers from further sets of bits of the bit sequence. The image decoding device comprises a mapping unit for generating a map for each identifier referenced in the dictionary, in which each map comprises the quantification values assigned to the corresponding identifier by the image data decoder to represent a presence, a proportion and/or a significance at each image coordinate of a material or condition corresponding to that identifier.

Figure 2:
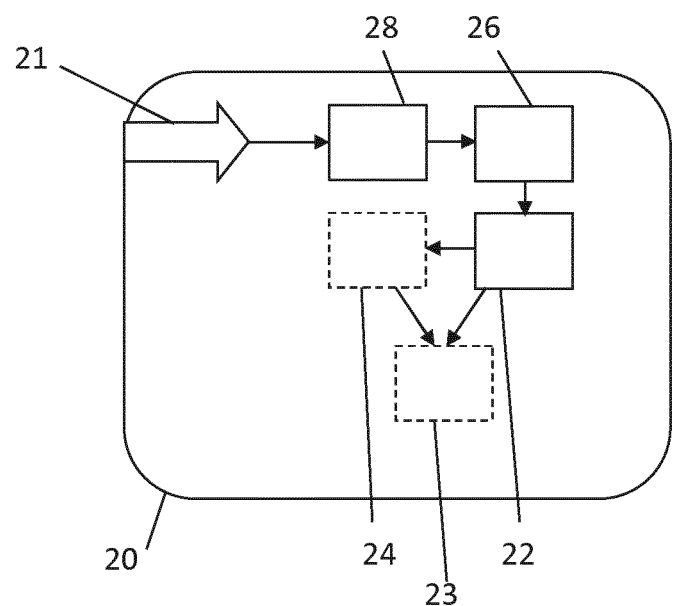
FIG. 2 schematically illustrates an image decoding device in accordance with embodiments of the present invention.

Referring to FIG. 2, an image decoding device 20 in accordance with embodiments of the present invention is shown. This image decoding device is adapted for decoding diagnostic image data packed in a diagnostic image format comprising metadata, e.g. as may be provided by a device in accordance with embodiments of the first aspect of the present invention.

The image decoding device 20 comprises a data input 21 for receiving the packed diagnostic image data, e.g. in a diagnostic image format, such as a DICOM format.

The image decoding device 20 comprises a data unpackager 28 for unpacking an encoded image from the packed diagnostic image data and for unpacking a dictionary from the metadata in the packed diagnostic image data.

The data unpackager 28 may be adapted for applying a decompression algorithm to decompress the encoded image from the packed diagnostic image data in the diagnostic image format.

The image decoding device 20 comprises an image data decoder 26 for decoding the encoded image such as to provide diagnostic image data. The image data decoder is adapted for, for each image coordinate, retrieving a bit sequence from the encoded image, identifying a subset of identifiers by looking up a subset identification index, encoded in a first set of bits of the bit sequence, in the dictionary, and for determining quantification values assigned to the identifiers from further sets of bits of the bit sequence.

For example, the image data decoder 26 may be adapted for determining the quantification values, e.g. volume fractions, by using the first set of bits, e.g. at the start of the bit sequence or another predetermined bit range in the bit sequence, e.g. a predetermined set of ceiling($\log_2$ S) bits, to identify a subset of identifiers, e.g. a material sequence, using a correspondence between a subset identifier index encoded by this first set of bits and the subset of identifiers, as defined in the dictionary. Further sets of bits of the bit sequence may encode quantification values, e.g. volume fractions of materials, e.g. in an order defined by the subset of identifiers in the dictionary.

The image data decoder 26 may be adapted for computing a further quantification value, e.g. for a last identifier in the subset of identifiers, by subtracting the sum of the quantification values encoded in the further sets of bits of the bit sequence from a predetermined value, e.g. a unit value, e.g. 1.

The image decoding device 20 comprises a mapping unit 22 for generating a map for each identifier referenced in the dictionary, each map comprising the quantification values assigned to the corresponding identifier by the image data decoder 26 to represent a presence, a proportion and/or a significance at each image coordinate of a material or condition corresponding to the identifier.

The image decoding device 20 may comprise a processing unit 24 for attributing further physical properties to each image coordinate, e.g. to each pixel or voxel, based on the maps generated by the mapping unit 12. For example, the quantification values may be representative of volume fractions of materials, and the further physical properties may be representative of mass fractions and/or numbers of units. For example, a mass fraction may be calculated by:

$$(\text{Mass } Frac.)_i = \frac{(Vol.\ Frac.) \times \rho_i}{Tot.\ Mass}$$

where Tot. Mass=$\sum_{i=1}^{m}$(Vol. Frac.)×$\rho_i$ and $\rho_i$ is a reference density of the $i^{th}$ material of the material sequence identified by the subset of identifiers. For example, such reference densities may be obtained from the metadata.

For example, a number of units may be calculated by:

$$(\#\ \text{units})_i = \frac{(\text{Mass } Frac.)_i \times \text{Voxel } Vol.}{(\text{Molecular Weight})_i}$$

where (Molecular Weight), is a reference molecular weight of the $i^{th}$ material of the material sequence identified by the subset of identifiers, and VoxelVol. is a reference volume of a voxel unit. For example, such reference molecular weights may be obtained from the metadata.

The image decoding device 20 may comprise a visualization unit 23 for showing a visual representation of at least one of the maps to a user, e.g. a radiologist. For example, the visualization unit may be adapted for providing a graphical user interface to the user for viewing the visual representation, e.g. in the form of an image.

The visualization unit 23 may be adapted to enable the user to select a specific point, e.g. a voxel or pixel, or a region of interest (ROI) on the visual representation, e.g. using visualization and selection tools as known in the art.

For example, during a conventional radiology diagnostic reading procedure, e.g. while examining standard CT images, the radiologist may be enabled to select a specific point or region of interest ROI) on the image using standard visualization tools.

For example, the visualization unit 23 may be adapted to select a homogeneous region in the selected ROI and/or a homogeneous region around the selected point. The homogeneous region may be selected according to statistical properties of the quantification values and/or the further physical properties.

The visualization unit 23 may be adapted for extracting data from the maps, e.g. multi-material data, and/or the further physical properties corresponding to the selected point, the selected ROI and/or the selected homogeneous region. The visualization unit 23 may be adapted for presenting the extracted data to the user. The visualization unit 23 may be adapted for providing material classification and/or quantification statistical information relating to the selected point or ROI, e.g. based on the extracted data, to the user.

Figure 3:
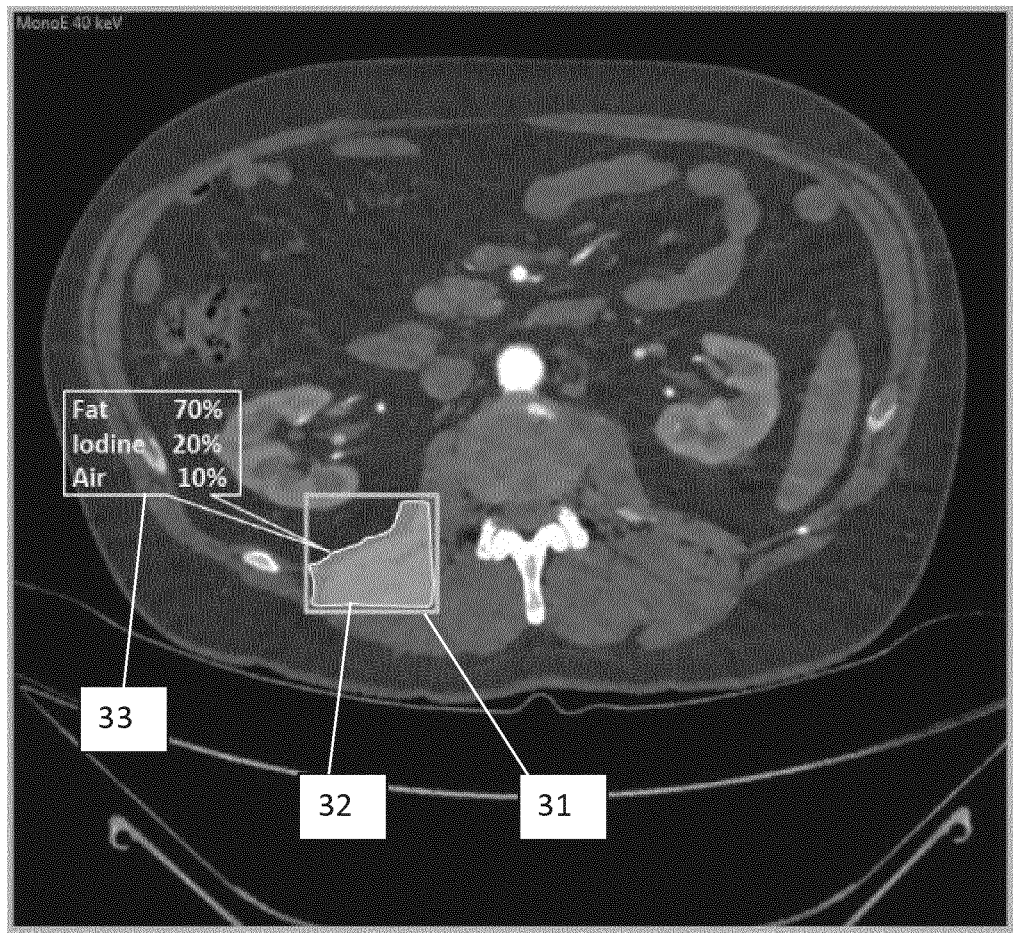
FIG. 3 illustrates an exemplary visualization relating to embodiments of the present invention.

For example, FIG. 3 shows an exemplary visualization in accordance with embodiments of the present invention. A homogeneous region 32 is determined in a selected region of interest 31, and a material classification 33 is presented to the user based on the extracted data.

The image decoding device 20 may be a workstation, e.g. a diagnostic imaging workstation. For example, embodiments of the present invention may relate to a workstation comprising an image decoding device in accordance with embodiments of the second aspect of the present invention. Such workstation may be adapted for enabling a user, e.g. a radiologist, to view and evaluate the diagnostic image data, after being received in an encoded and packed form via a digital communication network, e.g. from a PACS system.

In a third aspect, embodiments of the present invention also relate to a spectral computed tomography system comprising an image processing device in accordance with embodiments of the first aspect of the present invention and/or an image decoding device in accordance with embodiments of the second aspect of the present invention. For example, embodiments of the present invention may relate to a spectral computed tomography system such as the imaging system 100 described hereinbelow in relation to FIG. 5.

Figure 5:
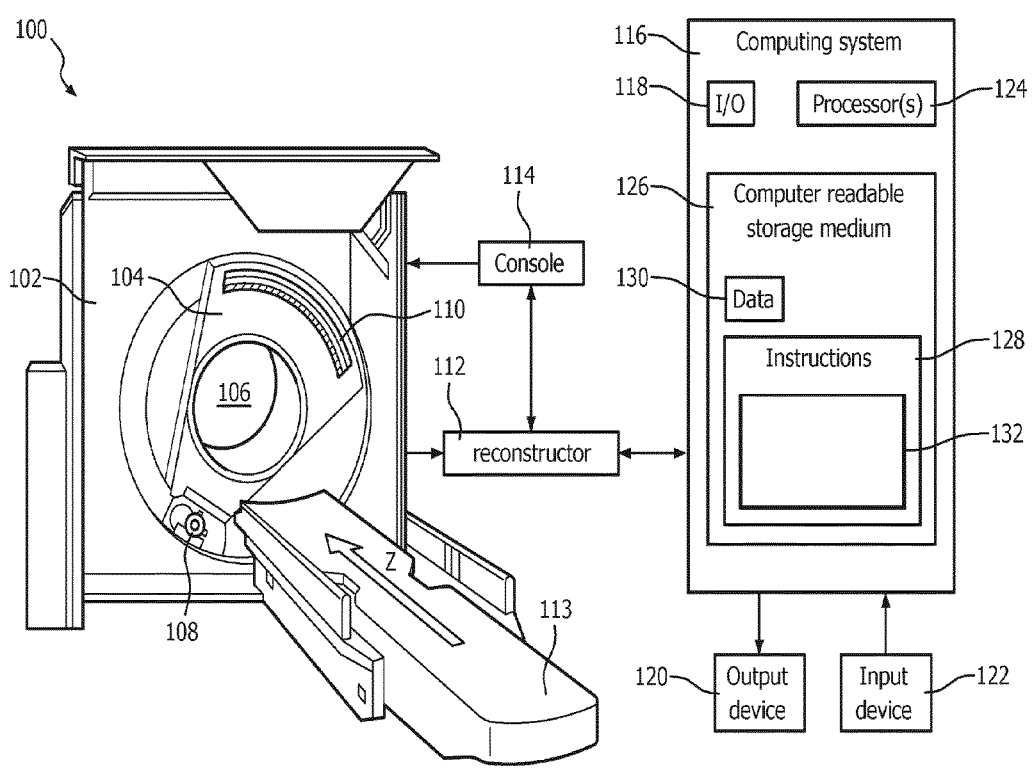
FIG. 5 illustrates a system in accordance with embodiments of the present invention.

FIG. 5 illustrates an imaging system 100 comprising a spectral computed tomography (Spectral CT) scanner. The imaging system 100 may comprise a generally stationary gantry 102 and a rotating gantry 104. The rotating gantry 104 may be rotatably supported by the stationary gantry 102 and may rotate around an examination region 106 about a longitudinal axis Z.

A radiation source 108, such as an x-ray tube, may be rotatably supported by the rotating gantry 104, e.g. such as to rotate with this rotating gantry 104, and may be adapted for emitting poly-energetic radiation that traverses the examination region 106. The radiation source 108 may comprise, or consist of, a single broad spectrum x-ray tube. Alternatively, the radiation source may be adapted for controllably switching between at least two different photon emission spectra, e.g. switching between at least two different peak emission voltages, such as 80 kVp, 140 kVp, etc., during scanning. In another variation, the radiation source 108 may comprise two or more x-ray tubes configured to emit radiation with different mean spectrums. In another variation, the radiation source 108 may comprise a combination of the above.

A radiation sensitive detector array 110 may subtend an angular arc opposite the radiation source 108 across the examination region 106. The array 110 may include one or more rows of detectors arranged with respect to each other along the Z-axis direction. The array 110 may be adapted for detecting radiation traversing the examination region 106, and generating signals indicative thereof. The array 110 may comprise a dual-energy detector with at least two radiation sensitive detector elements having different x-ray energy sensitivities, e.g. at least two scintillators and at least two corresponding photosensors having corresponding optical sensitivities. The radiation sensitive detector array 110 may alternatively or additionally comprise a direct conversion detector, such as a CdTe, CdZnTe or other direct conversion detector known in the art.

The system may comprise a reconstructor 112 for reconstructing the signals output by the detector array 110. This may include decomposing the signal into various energy dependent components. The reconstructor 112 may be adapted for reconstructing the energy dependent components and generating one or more images corresponding to one or more different energies. The reconstructor 112 may also combine the energy dependent components to generate non-spectral image data.

The system may comprise a subject support 113, such as a couch, for supporting an object or subject in the examination region. The system may also comprise an operator console 114, e.g. a general purpose computer programmed for controlling or monitoring the system 100 and/or for providing a user interface for an operator. The console 114 may include a human readable output device such as a monitor or display and an input device such as a keyboard and mouse. Software resident on the console 114 may allow the operator to interact with the scanner 100 via a graphical user interface (GUI) or otherwise. This interaction may include selecting a spectral imaging protocol or a non-spectral imaging protocol, initiating scanning, etc.

The imaging system 100 may be operably connected to a storage system and/or a server, e.g. a PACS system, e.g. computing system 116, such as a computer, that may comprise an input/output (I/O) interface 118 for facilitating communication with the spectral CT scanner. The imaging system 100 may comprise the computing system 116 as a system-level integrated component, or the imaging system 100 may be adapted for communicating with a stand-alone computing system 116, e.g. to transmit image data to the computing system 116.

The computing system 116 may further comprise an output device 120. The output device or output devices may comprise, for example, a display monitor, a film printer, a paper printer and/or an audio output for audio feedback. The computing system may also comprise an input device 122 or input devices, such as a mouse, a keyboard, a touch interface and/or a voice recognition interface. The computing system 116 may also comprise at least one processor 124, such as a central processing unit (CPU), a microprocessor, a dedicated application-specific integrated circuit (ASIC) for processing and/or an appropriately configured programmable hardware processor such as a field-programmable gate array. The computing system may comprise a computer readable storage medium 126, e.g. a non-transitory memory such as a physical digital memory. The computer readable storage medium 126 may store computer readable instructions 128 and data 130. The at least one processor 124 may be adapted for executing the computer readable instructions 128. The at least one processor 126 may also execute computer readable instructions carried by a signal, carrier wave or other transitory medium. Alternatively or additionally, the at least one processor may be physically configured to embody the instructions 128, e.g. entirely or in part, without necessarily requiring memory storage of these instructions, e.g. by configuration of a field-programmable gate array or an ASIC specifically designed to carry out at least a part of the instructions.

The computing system may be programmed, e.g. in accordance with the computer readable instructions referred to hereinabove, to implement an image processing device 10 in accordance with embodiments of the first aspect of the present invention.

The instructions 128 may comprise an image processing algorithm 132 for performing a method in accordance with embodiments of a fourth aspect of the present invention.

The system may furthermore comprise a workstation, e.g. a further computing system, e.g. similar to the computing system 116, in which instructions, e.g. similar to instructions 128, may comprise an algorithm for performing a method in accordance with embodiments of the present invention. The further computing system, such as a computer, may comprise an input/output (I/O) interface for facilitating communication with the computing system 116. The imaging system 100 may comprise the further computing system as a system-level integrated component, or the imaging system 100 may be adapted for communicating with a stand-alone further computing system, e.g. to transmit image data to the further computing system.

Figure 4:
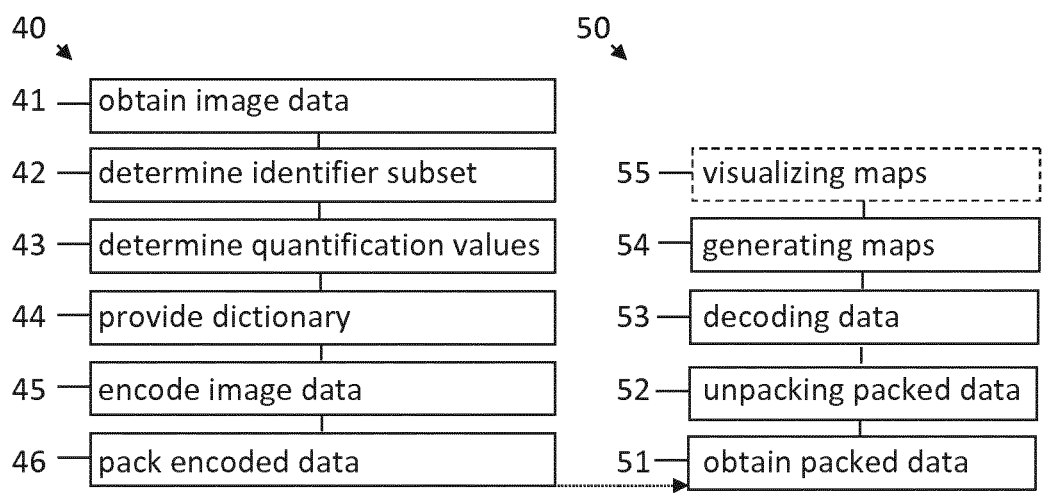
FIG. 4 illustrates methods in accordance with the present invention.

In a fourth aspect, the present invention relates to a method for processing diagnostic image data. Referring to FIG. 4, an exemplary method 40 in accordance with embodiments of the present invention is shown. The method 40 comprises obtaining 41 vector-valued diagnostic image data and, for each image coordinate of a plurality of image coordinates in the diagnostic image data, determining 42 a subset of identifiers, selected from a predetermined set of template identifiers, based on the received vector-valued diagnostic image data. The method comprises determining 43 for each identifier of the subset of identifiers a corresponding quantification value indicative of a presence, a proportion and/or a significance at the corresponding image coordinate of a material or condition corresponding to the identifier.

The method also comprises providing 44 a dictionary by assigning a subset identification index to each unique subset of identifiers that is determined by the quantification unit for the vector-valued diagnostic image data.

The method furthermore comprises encoding 45 the diagnostic image data such as to provide an encoded image, in which, for each image coordinate, e.g. for each pixel or voxel, a bit sequence is calculated, such that a first set of bits of the bit sequence encodes the subset identification index assigned to the subset of identifiers determined for the image coordinate and further sets of bits of the bit sequence respectively encode quantification values determined for the image coordinate.

The method comprises packing 46 the encoded image in a diagnostic image format comprising metadata and including the dictionary in the metadata.

A device in accordance with embodiments of the first aspect of the present invention may implement a method in accordance with embodiments of the fourth aspect of the present invention. Details relating to, and/or essential or optional features of, a method in accordance with embodiments of the fourth aspect of the present invention will be clear from the description provided hereinabove relating to the first aspect of the present invention. In a fifth aspect, the present invention also relates to a method for decoding diagnostic image data packed in a diagnostic image format comprising metadata. Referring to FIG. 4, an exemplary method 50 in accordance with embodiments of the present invention is shown.

The method 50 comprises obtaining 51 packed diagnostic image data, e.g. as provided by a method 40 in accordance with embodiments of the fourth aspect of the present invention, and unpacking 52 an encoded image from the packed diagnostic image data and unpacking a dictionary from metadata in the packed diagnostic image data.

The method 50 furthermore comprises decoding 53 the encoded image such as to provide diagnostic image data, in which, for each image coordinate, a bit sequence is retrieved from the encoded image, a subset of identifiers is identified by looking up a subset identification index, encoded in a first set of bits of the bit sequence, in the dictionary, and quantification values assigned to the identifiers are determined from further sets of bits of the bit sequence.

The method 50 also comprises generating a map 54 for each identifier referenced in the dictionary, each map comprising the quantification values assigned to the corresponding identifier by the image data decoder to represent a presence, a proportion and/or a significance at each image coordinate of a material or condition corresponding to the identifier.

The method 50 may comprise visualizing 55 at least one of the generated maps.

A device in accordance with embodiments of the second aspect of the present invention may implement a method in accordance with embodiments of the fifth aspect of the present invention. Details relating to, and/or essential or optional features of, a method in accordance with embodiments of the fifth aspect of the present invention will be clear from the description provided hereinabove relating to the second aspect of the present invention. In a sixth aspect, embodiments of the present invention also relate to a computer program product for, if implemented on a processing unit, performing a method in accordance with embodiments of the present invention, e.g. embodiments of the fourth and/or fifth aspect of the present invention.

In a seventh aspect, embodiments of the present invention also relate to a data carrier storing a computer program product in accordance with embodiments of the sixth aspect of the present invention.

In an eighth aspect, embodiments of the present invention also relate to a transmission of a computer program product in accordance with embodiments of the sixth aspect of the present invention over a digital communication network.

In a ninth aspect, embodiments of the present invention also relate to an encoded image in a diagnostic image format comprising metadata, wherein the metadata comprises a dictionary for assigning subset identification indices to a plurality of unique subsets of identifiers, and wherein the encoded image further comprises, e.g. in a compressed or uncompressed form, a bit sequence for each of a plurality of image coordinates, e.g. for each pixel or voxel in the image. The bit sequence comprises a first set of bits encoding a subset identification index for assigning one of the subsets of identifiers to that image coordinate, and further sets of bits that respectively encode quantification values determined for that image coordinate. Each quantification value is indicative of a presence, a proportion and/or a significance at the corresponding image coordinate of a material or condition corresponding to the identifier it is associated with. The diagnostic image format may be compliant with a DICOM format standard.

The encoded image may be an encoded image obtainable by a method in accordance with embodiments of the fourth aspect of the present invention. The encoded image may be an encoded image as may be provided by a device in accordance with embodiments of the first aspect of the present invention.

The invention claimed is:

1. An image processing device for processing diagnostic image data, the image processing device comprising:
   a data input for receiving vector-valued diagnostic image data;
   a quantification unit for, for each image coordinate of a plurality of image coordinates in said diagnostic image data, determining a subset of m material identifiers, each material identifier being indicative of materials contained in the imaged object at a location represented by that image coordinate, selected from a predetermined set of $N_m$ known template material identifiers wherein $N_m>m$, based on the received vector-valued diagnostic image data and determining for each material identifier of said subset of material identifiers a corresponding quantification value indicative of a presence, a proportion and/or a significance at said image coordinate of a material or condition corresponding to said material identifier, wherein said quantification unit is adapted for determining said subset of material identifiers by selecting said subset of material identifiers from a plurality of S template subsets of said plurality of template material identifiers, the plurality of S template subsets each having a unique specific sequence of material identifiers;
   a dictionary definition unit for providing a dictionary, said dictionary definition unit being adapted for assigning a subset identification index to each unique subset of material identifiers that is determined by the quantification unit for the vector-valued diagnostic image data and for including a definition of each of said assignations in said dictionary;
   an image data encoder for encoding the diagnostic image data such as to provide an encoded image, said image data encoder being adapted for, for each image coordinate, calculating a bit sequence, such that a first set of bits of said bit sequence encodes the subset identification index assigned to the subset of material identifiers determined for said image coordinate and further sets of bits of said bit sequence respectively encode quantification values determined for said image coordinate; and
   a data packager for packing said encoded image in a diagnostic image format comprising metadata, and for inserting said dictionary into said metadata,
   wherein said image data encoder is adapted for determining said first set of bits as a binary representation of said subset identification index in a number of bits equal to the least succeeding integer greater than or equal to the base-2 logarithm of the number of template subsets in said plurality of S template subsets.

2. The image processing device of claim 1, wherein said data input is adapted for receiving spectral computed tomography volumetric image data, magnetic resonance volumetric image data and/or nuclear medicine tomography volumetric image data.

3. The image processing device of claim 1, wherein said plurality of template identifiers comprises template identifiers representative of different materials and/or chemical elements, wherein said quantification unit comprises a material decomposition processor for determining properties of different materials based on the vector-valued diagnostic image data for each image coordinate such as to determine said quantification value as a value indicative of a volume fraction of a material identified by said identifier in a volume represented by said image coordinate.

4. The image processing device of claim 1, wherein said image data encoder is adapted for determining said further sets of bits of the bit sequence by encoding said quantification values in an order defined by said dictionary, wherein each further set of bits consists of a number of bits equal to the least succeeding integer greater than or equal to the base-2 logarithm of the inverse of a precision value.

5. The image processing device of claim 4, wherein said quantification unit is adapted for determining said quantification values such that the sum of the quantification values determined for each subset of identifiers equals a predetermined value, wherein said further sets of bits encode said quantification values for all but one identifier in the determined subset of identifiers.

6. The image processing device of claim 1, wherein said data packager is adapted for applying a compression algorithm to compress said encoded image and for including said compressed encoded image in said diagnostic image format.

7. The image processing device of claim 1, wherein said data packager is adapted for generating an output diagnostic image in said diagnostic image format, wherein said diagnostic image format is compliant with a DICOM standard.

8. A Picture Archiving and Communication System and/or diagnostic image portal system comprising an image processing device in accordance with claim 1.

9. An image decoding device for decoding diagnostic image data packed in a diagnostic image format comprising metadata, the image decoding device comprising:
    a data input for receiving said packed diagnostic image data;
    a data unpackager for unpacking an encoded image from said packed diagnostic image data and a dictionary from metadata in said packed diagnostic image data;
    an image data decoder for decoding said encoded image such as to provide diagnostic image data, said image data decoder being adapted for, for each image coordinate, retrieving a bit sequence from said encoded image, identifying a subset of identifiers by looking up a subset identification index, encoded in a first set of bits of said bit sequence, in said dictionary, and for determining quantification values assigned to said identifiers from further sets of bits of said bit sequence, wherein said first set of bits is a binary representation of said subset identification index in a number of bits equal to the least succeeding integer greater than or equal to the base-2 logarithm of a number of template subsets in a plurality of S template subsets; and
    a mapping unit for generating a map for each identifier referenced in said dictionary, each map comprising said quantification values assigned to the corresponding identifier by said image data decoder to represent a presence, a proportion and/or a significance at each image coordinate of a material or condition corresponding to said identifier.

10. The image decoding device of claim 9, wherein said image data decoder is adapted for determining said quantification values by decoding further sets of bits of said bit sequence that encode quantification values in an order defined by said subset of identifiers in said dictionary, and for computing a further quantification value for a last identifier in said subset of identifiers by subtracting the sum of said quantification values encoded in said further sets of bits from a predetermined value.

11. The image decoding device of claim 9, comprising a processing unit for attributing further physical properties to each image coordinate based on said maps generated by said mapping unit.

12. The image decoding device of claim 9, comprising a visualization unit for showing a visual representation of at least one of said maps to a user, said visualization unit being adapted for providing a graphical user interface to said user for viewing said visual representation, wherein said visualization unit is adapted to enable the user to select a specific point and/or a region of interest on said visual representation, for determining a homogeneous region in the selected region of interest and/or around said selected point, for extracting data from said maps corresponding to said determined homogeneous region, and for presenting a material classification and/or quantification statistical information relating to the determined homogeneous region to said user.

13. A method for processing diagnostic image data, the method comprising:
    obtaining vector-valued diagnostic image data;
    for each image coordinate of a plurality of image coordinates in said diagnostic image data, determining a subset of identifiers, selected from a predetermined set of template identifiers, based on the received vector-valued diagnostic image data;
    determining for each identifier of said subset of identifiers a corresponding quantification value indicative of a presence, a proportion and/or a significance at said image coordinate of a material or condition corresponding to said identifier;
    providing a dictionary by assigning a subset identification index to each unique subset of identifiers that is determined by the quantification unit for the vector-valued diagnostic image data;
    encoding the diagnostic image data such as to provide an encoded image, wherein, for each image coordinate, a bit sequence is calculated such that a first set of bits of said bit sequence encodes the subset identification index assigned to the subset of identifiers determined for said image coordinate and further sets of bits of said bit sequence respectively encode quantification values determined for said image coordinate;
    determining said first set of bits as a binary representation of said subset identification index in a number of bits equal to the least succeeding integer greater than or equal to the base-2 logarithm of a number of template subsets in a plurality of S template subsets; and
    packing said encoded image in a diagnostic image format comprising metadata and including said dictionary in said metadata.

* * * * *